United States Patent
Hrnicek et al.

(10) Patent No.: US 10,792,094 B2
(45) Date of Patent: Oct. 6, 2020

(54) CONTINUOUS COMPOUND CURVED TIP FOR CANNULATION

(71) Applicant: Cook Medical Technologies LLC, Bloomington, IN (US)

(72) Inventors: Jillian Hrnicek, Avada, CO (US); Vihar C. Surti, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 431 days.

(21) Appl. No.: 14/450,602

(22) Filed: Aug. 4, 2014

(65) Prior Publication Data

US 2015/0045776 A1  Feb. 12, 2015

Related U.S. Application Data

(60) Provisional application No. 61/863,591, filed on Aug. 8, 2013.

(51) Int. Cl.
| | |
|---|---|
| *A61B 18/14* | (2006.01) |
| *A61B 1/012* | (2006.01) |
| *A61B 1/018* | (2006.01) |
| *A61M 25/00* | (2006.01) |
| *A61M 25/01* | (2006.01) |

(52) U.S. Cl.
CPC .......... *A61B 18/1477* (2013.01); *A61B 1/012* (2013.01); *A61B 1/018* (2013.01); *A61M 25/0041* (2013.01); *A61M 25/0082* (2013.01); *A61M 25/0108* (2013.01); *A61B 1/0125* (2013.01); *A61M 2210/1042* (2013.01); *A61M 2210/1075* (2013.01)

(58) Field of Classification Search
CPC .......... A61M 25/0041; A61M 25/0152; A61M 2210/1042; A61M 2210/1075; A61M 25/0082; A61M 25/0108; A61B 18/1477; A61B 1/012; A61B 1/0125; A61B 1/018
See application file for complete search history.

(56) References Cited

U.S. PATENT DOCUMENTS

| | | |
|---|---|---|
| 5,589,120 A | 12/1996 | Khan et al. |
| 5,603,704 A | 2/1997 | Brin et al. |
| 5,626,136 A | 5/1997 | Webster, Jr. |
| 5,916,214 A | 6/1999 | Cosio et al. |
| 5,931,811 A | 8/1999 | Haissaguerre et al. |

(Continued)

FOREIGN PATENT DOCUMENTS

| | | | | |
|---|---|---|---|---|
| EP | 1484078 A1 | * | 12/2004 | ........ A61M 25/0041 |
| WO | WO 2007/136829 A1 | | 11/2007 | |
| WO | WO 2007136829 A1 | * | 11/2007 | ............. A61B 17/00 |

OTHER PUBLICATIONS

Udd, M.; Kylänpää, L.; Halttunen, J. "Management of Difficult Bile Duct Cannulation in ERCP," *World J Gastrointest Endosc*, 2010, 2, 97-103.

*Primary Examiner* — Lee S Cohen
*Assistant Examiner* — Tigist S Demie
(74) *Attorney, Agent, or Firm* — Brinks Golson & Lione

(57) ABSTRACT

A catheter is described for use in cannulating a bile duct in ERCP or sphincterotomy procedures. The catheter has a continuous compound curve that has first and second curves. The first and second curves have radii of curvature and lengths that orient the tip of the catheter selectively toward a bile duct.

19 Claims, 3 Drawing Sheets

(56) References Cited

U.S. PATENT DOCUMENTS

| | | | | |
|---|---|---|---|---|
| 5,971,974 | A * | 10/1999 | Keisz | A61M 25/0041 604/264 |
| 6,190,353 | B1 * | 2/2001 | Makower | A61B 1/3137 604/95.01 |
| 7,462,184 | B2 * | 12/2008 | Worley | A61M 25/0041 604/532 |
| 8,100,903 | B2 | 1/2012 | Kennedy, II | |
| 8,231,613 | B2 * | 7/2012 | Baxter | A61B 18/1492 606/20 |
| 2003/0114833 | A1 | 6/2003 | Thompson et al. | |
| 2003/0130679 | A1 * | 7/2003 | Aliperti | A61B 18/14 606/170 |
| 2005/0222557 | A1 * | 10/2005 | Baxter | A61B 18/1492 606/16 |
| 2007/0282358 | A1 | 12/2007 | Remiszewski et al. | |
| 2009/0043259 | A1 | 2/2009 | Hardin, Jr. et al. | |
| 2009/0264980 | A1 | 10/2009 | Mackay | |
| 2010/0057077 | A1 * | 3/2010 | Ducharme | A61B 18/14 606/39 |

* cited by examiner

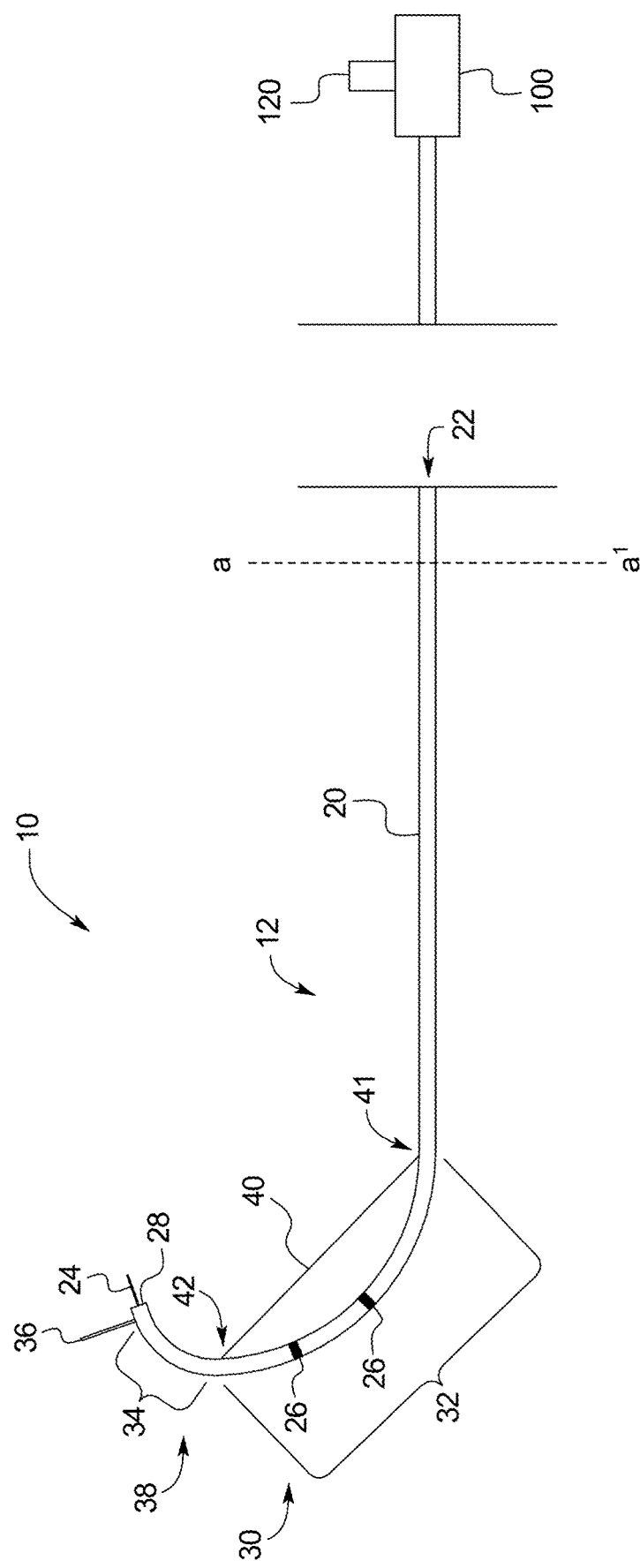

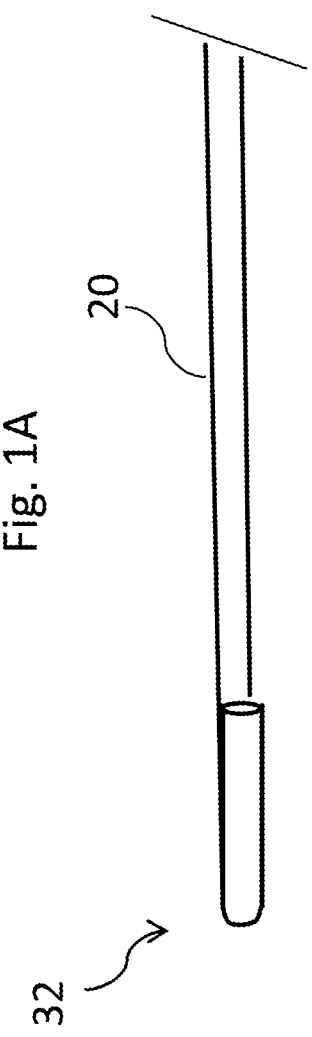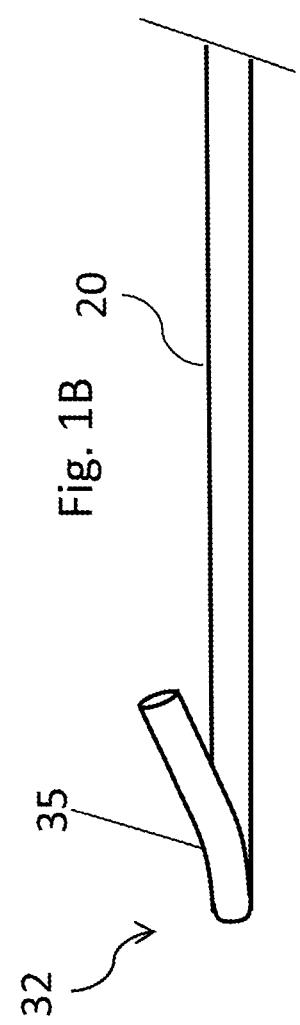

CONTINUOUS COMPOUND CURVED TIP FOR CANNULATION

RELATED APPLICATIONS

The present patent document claims the benefit of the filing date under 35 U.S.C. § 119(e) of Provisional U.S. Patent Application Ser. No. 61/863,591, filed Aug. 8, 2013, which is hereby incorporated by reference.

TECHNICAL FIELD

The present invention relates to an endoscopic device having a continuous compound curve for selective cannulation of the bile duct.

BACKGROUND OF THE INVENTION

Gastrointestinal endoscopy is commonly used to gain access to the digestive tract for the purpose of incising and cauterizing tissue. Many common endoscopy procedures exist for achieving this purpose.

Endoscopic retrograde cholangiopancreatography (ERCP) is a technique that uses both endoscopy and fluoroscopy for the diagnosis and treatment of medical conditions of the biliary or pancreatic ductal systems such as gallstones, strictures, blocked bile ducts, or the placement of a stent. In an ERCP procedure, a physician employs an endoscope with an ERCP cannula to gain access to the area of the biliary tree. One of the most significant challenges in ERCP is directing a wire guide into the appropriate duct. In bile duct cannulation, the primary concern is to access the bile duct, while avoiding the pancreatic duct due to the potential for post-ERCP pancreatitis. Pancreatitis is the most common complication of ERCP. If a physician has to attempt to cannulate the bile duct multiple times, the risk of pancreatitis increases.

Endoscopic sphincterotomy is a specific procedure in which a sphincterotome is used in combination with an endoscope to surgically cut a patient's sphincter. As one example, the sphincterotome may be used to partially cut open the duodenum at the Papilla of Vater to access the common bile duct and remove bile duct stones which form an obstruction therewithin. Conventional sphincterotomes utilized in this technique can create major complications, including bleeding, pancreatitis, perforation, and cholangitis.

In view of these drawbacks of current technology, there is an unmet need for bile duct cannulas that can controllably and reliably access the bile duct while avoiding the pancreatic duct.

SUMMARY OF THE INVENTION

This invention provides a catheter having a distal end portion with a continuous compound curve in order to assist in cannulation of the bile duct during ERCP procedures or sphincterotomies. The second curve of the compound curve has a more acute angle so that a wire guide may exit the catheter at the proper angle to point towards the bile duct and away from the pancreatic duct. One of the most significant challenges in ERCP is directing the wire guide into the appropriate duct. This invention aims to mitigate some of the challenges associated with cannulation. This compound curved tip may also give a better angle for going through the papilla.

In one aspect of the invention is provided an endoscopic device for cannulation of a bile duct having a continuous compound curved tip. The device includes a tubular member having a shaft, a distal end portion, and optionally a lumen extending through at least a portion of the tubular member. The distal end portion has a continuous compound curve portion, where the compound curve has a first curved portion and a second curved portion. The first curved portion lies proximal to the second curved portion with the two portions being connected to form a continuous compound curve. The radius of curvature of the first curved portion is greater than the radius of curvature of the second curved portion. In certain embodiments, the first curved portion has a radius of curvature of about 0.7 to about 1.5 inches. In other embodiments, the second curved portion has a radius of curvature of about 0.15 to about 0.5 inches. In certain embodiments, the distal end portion includes a substantially straight end segment. The radii of curvature and the lengths of the first and second curved portions, together, are adapted to position the distal end portion in a patient's duodenum through the papilla of Vater with the tip of the distal end portion oriented toward the patient's bile duct and away from the pancreatic duct.

In one embodiment, the invention provides an ERCP catheter having a distal end portion with a continuous compound curve portion. In another embodiment, the invention provides a sphincterotome having a cutting wire and a distal end portion with a continuous compound curve portion.

BRIEF DESCRIPTION OF THE DRAWINGS

FIG. 1 shows an exemplary embodiment of an endoscopic device with a distal end having a continuous compound curved tip.

FIG. 1A shows an exemplary embodiment of an endoscopic device of the invention having a co-planar arrangement of the shaft 20 and the first curved portion 32 with the curve of the distal end portion shown facing forward in the plane of the device.

FIG. 1B shows an exemplary embodiment of an endoscopic device of the invention with the curve of the distal end portion shown facing forward where the first curved portion 32 has a deflection 35 out of the plane of the shaft.

DETAILED DESCRIPTION

Figure 3:
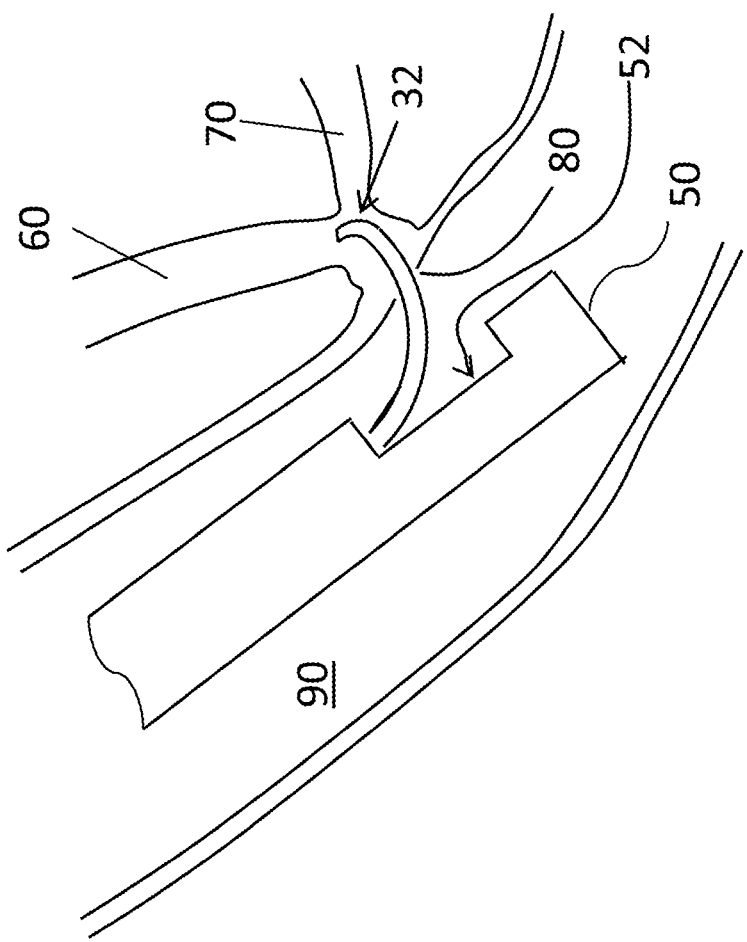
FIG. 3 is a side view of the compound curved tip emerging from an opening at the distal end of an endoscope with the distal tip oriented toward the bile duct.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

An exemplary embodiment of a curved tip catheter 10 of the invention is shown in FIG. 1. The catheter 10 includes a tubular member 12 having a shaft 20 and a distal end portion 30, which has a continuous compound curve 38. The continuous compound curve 38 is made up of a first curved portion 32 and a second curved portion 34. In the embodiment of FIG. 1, the distal end portion includes an optional substantially straight end segment 36 and a wire guide 24 extending distally from the distal tip 28. The catheter also includes a control handle 100. Optional radiopaque marker bands 26 may be thermally bonded or crimped about the distal end portion to enable fluoroscopic visualization of the distal end portion 30 as it is being maneuvered. The catheter, including the distal end portion, first and second curved portions, and the end segment may be tapered or non-tapered. The walls of the catheter may be of varying thickness.

Figure 2:
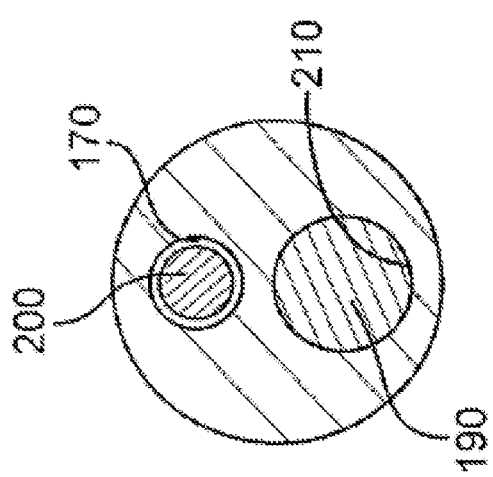
FIG. 2 is a cross-sectional view of FIG. 1 taken along line a-a' showing a wire guide extending through one of the lumens of the sphincterotome and an electrical conductor extending through the other lumen.

In certain embodiments, a wire guide lumen extends through at least a portion of the distal end portion. In general, the tubular member may have a single lumen, or multiple lumens, i.e., two or more lumens. FIG. 2 shows a cross-sectional view of the tubular member along the line a-a'. In the embodiment in FIG. 2, the tubular member has two lumens. Lumen 210 is adapted to receive a wire guide 24, that may be movably disposed within the wire guide lumen. The lumen 210 may also be configured for the passage of fluids or contrast therethrough. Lumen 170 is adapted to receive an electrical conductor wire 200. Although the lumens 170 and 210 are shown with circular cross-sectional shapes, other lumen shapes are possible. The tubular member may also have more than two lumens. For example, a third lumen may be dedicated for the passage of fluids or contrast fluid therethrough.

The electrical conductor wire 200 transmits current to the cutting wire 40. The conductor wire 200 is a wire extending through lumen 170 (FIG. 2) and is connected at its proximal end to electrical connector 120 (FIG. 1) to provide a high frequency electrical current to conductor 200 and cutting wire 40 as is well known to one of ordinary skill in the art. Conductor 200 protrudes outward of the wall of tubular member 12 at the distal end portion 30 through first opening 41 to become cutting wire 40. The cutting wire 40 is bowed between the first opening 41 and the second opening 42, disposed outside of the wall of tubular member 12, along an inner radius of curvature of the first curved portion 32. The cutting wire 40 re-enters the wall of the tubular member 12 through second opening 42 and extends proximally through the lumen 170. The second opening 42 is located proximal to the second curved portion 34. The cutting wire may have various lengths by changing the proximal and distal openings 41 and 42.

Preferably, the conductor 200 and cutting wire 40 may be formed from a single wire. Alternatively, the cutting wire 40 and conductor 200 may be distinct components that may be connected to each other by soldering or other conventional means known in the art.

The compound curved tip catheter of the invention may be made from various materials including polytetrafluoroethylene (PTFE), fluorinated ethylene propylene (FEP), or other thermoplastic resins (e.g., polyurethane). Preferably the second curved portion, the compound curve portion and the catheter are made from PTFE. Where the compound curve portion is made from FEP, the curved tip may also be affixed to a catheter shaft made of PTFE using a standard heat bond.

The compound curved tip may be formed in two steps. In the first step, the second curved portion is formed by heat setting, for example using a die or mandrel. Following insertion into a die or mandrel, suitable heat and pressure may be applied for a given duration of time to heat set the second curved portion. In general, the second curved portion is formed by heating to a temperature sufficient for it to acquire the shape of the die/mandrel and retain that shape upon cooling. For example, the second curved portion may be formed with PTFE by heat setting at a temperature sufficient to soften the PTFE (e.g., around the melting temperature). The second curved portion formed in this manner permanently retains the curved form imparted by the heat setting process. In the second step of forming the compound curved tip, the first curved portion is formed using a conventional forming/shaping wire, as is well known in the art.

The first and second curved portions of the continuous compound curve have different center points and angles. The first curved portion has a larger radius of curvature than the second curved portion. In one aspect of the invention, the first curved portion has a radius of curvature of about 0.7 inch to about 1.5 inches and the second curved portion has a radius of curvature of about 0.15 to about 0.5 inch. The radii of curvature and the lengths of the first and second curved portions, together, are adapted to orient the distal tip of the distal end portion toward a bile duct and away from a pancreatic duct. In one embodiment of this aspect, the first curved portion has a length of about 1.5 inches to about 4.5 inches. In another embodiment, the second curved portion has a length of about 0.1 to about 0.35 inch. In another embodiment, the first curved portion has a radius of curvature of about 1 inch and a length of about 2.1 inches. In yet another embodiment, the second curved portion has a radius of curvature of about 0.25 inch and a length of about 0.13 inch.

According to any of the foregoing embodiments are still other embodiments where the radius of curvature and the length of the second curved portion form an arc of about 5 to about 60 degrees. In still other embodiments, the radius of curvature and the length of the second curved portion 34 form an arc of about 30 degrees.

The substantially straight end segment 36 extends beyond the second curved portion. The combined length of the substantially straight end segment and the second curved portion is about 0.15 to about 0.35 inch. Thus, the length of the substantially straight end portion may have any length up to about 0.25 inch. In one embodiment, the substantially straight end segment has a length of about 0.05 inch.

The invention encompasses various combinations among the curvatures and lengths given above for the first curved portion, the second curved portion, and the substantially straight end segment. For example, in one embodiment, the first curved portion has a radius of curvature of about 0.7 inch to about 1.5 inches and a length of about 1.5 to about 4.5 inches and the second curved portion has a radius of curvature of about 0.15 to about 0.5 inch and a length of about 0.1 to about 0.35 inch. In another embodiment, the first curved portion has a radius of curvature of about 1 inch and a length of about 2.1 inches and the second curved portion has a radius of curvature of about 0.15 to about 0.5 inch and a length of about 0.1 to about 0.35 inch. In another embodiment, the first curved portion has a radius of curvature of about 0.7 inch to about 1.5 inches and a length of about 1.5 to about 4.5 inches and the second curved portion has a radius of curvature of about 0.25 inch and a length of about 0.13 inch. In yet another embodiment, the first curved portion has a radius of curvature of about 1 inch and a length of about 2.1 inches and the second curved portion has a radius of curvature of about 0.25 inch and a length of about 0.13 inch.

The first curved portion and the second curved portion may be substantially co-planar or they may be oriented in different planes according to the needs of a particular medical procedure. Similarly, the first curved portion 32 may be substantially planar with the shaft as illustrated in FIG. 1A. Alternatively, as shown in FIG. 1B, the first curved portion may include a deflection 35 out of the plane formed by the shaft and any section of the first curved portion that is co-planar with the shaft. This arrangement gives the first curved portion a three-dimensional shape. The deflection may be a continuous deflection throughout the length of the first curved portion giving the first curved portion a spiral or partial spiral shape. Or, the first curved portion may have a single deflection with the more distal section of the first curved portion being substantially in one plane defined by the single deflection. Where the first curved portion includes a deflection out of the plane of the shaft, the distal tip may be deflected out of the plane formed by the shaft and any co-planar section of the first curved portion by any angle up to about 40-45 degrees. Thus, in this arrangement the distal tip, the first curved portion, and the shaft do not substantially occupy a single plane. Where the first curved portion has a three dimensional curve, the angle of deflection at the distal tip is preferably about 27 degrees. Throughout the deflection in the first curved portion, the radius of curvature of the first curved portion, as described herein, remains substantially unchanged.

In each of the embodiments described above, the first curved portion is adapted to deform from the stated radius of curvature when subjected to a straightening force. Upon removal of the straightening force, the first curved portion may return to its original curved form.

As illustrated in FIG. 3, an endoscope 50 is first positioned within a patient's duodenum 90 with the distal end of the endoscope near the duodenal papilla 80. The distal end portion of the tubular member is advanced within an accessory channel 52 of an endoscope 50. During advancement within the accessory channel, the first curved portion flexes into a semi-straightened shape. As the distal end portion emerges from the distal end of the accessory channel, it relaxes back to its pre-curved shape. The distal end portion is shown in FIG. 3 advanced through the duodenal papilla 80 with the second curved portion 32 orienting the tip of the catheter toward the bile duct 60 and away from the pancreatic duct 70. The selective orientation of the catheter tip toward the bile duct permits a wire guide to exit the tip of the catheter at an angle pointing toward the bile duct.

The second curved portion provides a better angle for selective cannulation of the bile duct compared to catheters lacking a continuous compound curve. This permits a physician to more readily cannulate the bile duct with fewer attempts, thereby cutting down on procedure time and repeated attempts to cannulate the bile duct that have been linked to pancreatitis.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

What is claimed is:

1. An endoscopic device comprising:
    a tubular member comprising a shaft, a distal end portion, and a wire guide lumen extending through at least a portion of the distal end portion;
    the distal end portion comprising a continuous compound curve portion and a distal tip;
    the continuous compound curve portion comprising a non-permanent first curved portion and a permanent second curved portion, each having a radius of curvature and a length, the first curved portion located proximal to the second curved portion, the second curved portion formed by heat setting to permanently retain the radius of curvature of the second curved portion upon cooling in a fixed position, and the first curved portion temporarily formed by using a forming/shaping wire, the first curved portion being movable upon the application of an external force, the first curved portion connected to the second curved portion to form a continuous compound curve wherein the radius of curvature of the first curved portion is greater than the radius of curvature of the second curved portion and the radii of curvature and the lengths of the first and second curved portions, together, are adapted to position the distal end portion in a patient's duodenum through the papilla of Vater with the tip of the distal end portion oriented toward the patient's bile duct and away from the pancreatic duct,
    wherein the endoscopic device further comprises an electrically conductive cutting element located along the distal end portion and proximal to the second curved portion, the cutting element connected to an electrical conductor extending within a second lumen extending through at least a portion of the tubular member, the cutting element extending exteriorly of the tubular member along an inner radius of curvature of the first curved portion, the cutting element being movable within a cutting plane and configured to apply the external force to the first curved portion so as to alter the radius of curvature of the first curved portion temporarily formed by the forming/shaping wire without altering the permanent radius of curvature of the second curved portion.

2. The device of claim 1, wherein the first curved portion has a radius of curvature of about 0.7 to about 1.5 inches and the second curved portion has a radius of curvature of about 0.15 to about 0.5 inches.

3. The device of claim 2, wherein the first curved portion has a length of about 1.5 to about 4.5 inches.

4. The device of claim 2, wherein the second curved portion has a length of about 0.1 to about 0.35 inches.

5. The device of claim 3, wherein the second curved portion has a length of about 0.1 to about 0.35 inches.

6. The device of claim 5, wherein the first curved portion has a radius of curvature of about 1 inch and a length of about 2.1 inches.

7. The device of claim 5, wherein the second curved portion has a radius of curvature of about 0.25 inch and a length of about 0.13 inch.

8. The device of claim 6, wherein the second curved portion has a radius of curvature of about 0.25 inch and a length of about 0.13 inch.

9. The device of claim 4, wherein the radius of curvature and the length of the second curved portion form an arc of about 30 degrees.

10. The device of claim 5, wherein the distal end portion further comprises a substantially straight end segment, the substantially straight end segment comprising the distal tip and being located at a distal end of the second curved portion.

11. The device of claim 10, wherein the substantially straight end segment has a length of about 0.05 inch.

12. The device of claim 8, wherein the distal end portion further comprises a substantially straight end segment, the substantially straight end segment comprising the distal tip and being located at a distal end of the second curved portion and having a length of about 0.05 inch.

13. The device of claim 1, wherein the first curved portion is adapted to deform from the radius of curvature of the first curved portion when subjected to a straightening force applied by the electrically conductive cutting element.

14. The device of claim 8, wherein the second curved portion is formed from polytetrafluoroethylene.

15. The device of claim 1 wherein the first curved portion is substantially co-planar with the shaft.

16. The device of claim 1 wherein the first curved portion comprises a deflection such that the distal tip, the first curved portion, and the shaft do not substantially occupy a single plane, wherein the first curved portion comprises a proximal segment and a distal segment, the proximal segment being disposed within a first plane coincident with the shaft, and the distal segment being disposed within a second plane that is different from the first plane, and further wherein the second curved portion is disposed within the second plane.

17. The device of claim 1 wherein the first curved portion and the second curved portion are substantially co-planar.

18. The device of claim 1 further comprising a radiopaque marker about the distal end portion of the tubular member.

19. The device of claim 1 further comprising a wire guide and an endoscope having an accessory channel extending therethrough, the tubular member being movably disposed within at least a portion of the accessory channel, the wire guide being movably disposed through the wire guide lumen and extending distally of the distal tip.

* * * * *